(12) United States Patent
Hammond, Jr. et al.

(10) Patent No.: US 7,252,013 B2
(45) Date of Patent: Aug. 7, 2007

(54) BRAZED JOINT TORQUE TEST APPARATUS AND METHODS

(75) Inventors: James A. Hammond, Jr., O'Fallon, MO (US); George E. Anderson, Alton, IL (US); Brian J. Martinek, Troy, MO (US)

(73) Assignee: The Boeing Company, Chicago, IL (US)

( * ) Notice: Subject to any disclaimer, the term of this patent is extended or adjusted under 35 U.S.C. 154(b) by 153 days.

(21) Appl. No.: 11/238,278

(22) Filed: Sep. 29, 2005

(65) Prior Publication Data
US 2007/0068277 A1  Mar. 29, 2007

(51) Int. Cl.
*G01N 3/02* (2006.01)
(52) U.S. Cl. .............. 73/856; 73/862.21; 73/862.22; 73/862.23
(58) Field of Classification Search .............. 73/856, 73/862.21–862.23
See application file for complete search history.

(56) References Cited

U.S. PATENT DOCUMENTS

| | | | |
|---|---|---|---|
| 5,312,097 A | * 5/1994 | Womack | 269/139 |
| 5,335,556 A | * 8/1994 | Mogilnicki | 73/862.21 |
| 6,742,403 B2 | * 6/2004 | Thomas | 73/862.21 |
| 6,945,340 B2 | * 9/2005 | Bise et al. | 175/430 |
| 7,114,714 B2 | * 10/2006 | Wong | 269/45 |
| 2003/0002940 A1 | * 1/2003 | Forth et al. | 408/226 |
| 2003/0115971 A1 | * 6/2003 | Thomas | 73/862.21 |
| 2005/0271890 A1 | * 12/2005 | Koecher | 428/615 |

\* cited by examiner

*Primary Examiner*—Edward Lefkowitz
*Assistant Examiner*—Freddie Kirkland, III
(74) *Attorney, Agent, or Firm*—Lee & Hayes, PLLC

(57) ABSTRACT

A method and device for testing a substantially cylindrical tool having an axis is performed by imparting a testing torque to the cylindrical tool. The tool is clamped in a vise. The tool has a driven end including a shank and a working end in opposed relation along the axis. The vise is configured to clamp the tool to prevent rotation of the tool about the axis. The shank is clamped in a chuck. The chuck has a adapter defining a void configured to engagingly receive a socket drive shaft. A torque wrench having a lever arm and a socket driver shaft is engaged by insertion of the socket drive shaft into the void. A torque is imparted to the cylindrical tool about its axis by suitably imparting a force on the lever arm. The quantum of torque imparted is measured based upon operation of the torque wrench.

20 Claims, 4 Drawing Sheets

FIG.1 *(PRIOR ART)*

BRAZED JOINT TORQUE TEST APPARATUS AND METHODS

FIELD OF THE INVENTION

This invention relates to methods and apparatus for torque-testing of brazed joints, including brazed joints for drill bits and the like.

BACKGROUND OF THE INVENTION

One of the most important and essential tools in any metalworking shop is the drilling machine or drill press. Although the drilling machine is used primarily for drilling holes, it is often used for reaming, boring, tapping, counterboring, countersinking, and spotfacing.

Drilling machines typically operate on the same basic principle. The spindle turns the cutting tool as the cutting tool is advanced either by hand or automatically into a workpiece that is mounted on the table or held in a drill press vise. Successful operation of drilling machines generally requires a good knowledge of the machine, proper set-up of the work, correct speed and feed, and proper use of cutting fluids applied to the cutting tool and work.

Referring to FIG. 1, a known drill 99 is an end-cutting tool for producing holes. The drill 99 has one or more cutting edges 91, and flutes 92 to allow fluids to enter and chips to be ejected. The drill 99 is composed of a shank 93, a body 94, and a point 95 at the cutting end of the drill 99. The shank 93 is the part of the drill 99 that is held and driven (e.g. by a drill motor) and may be straight or tapered. The body 94 of the drill extends from the shank 93 to the point 95, and contains the flutes 92. During sharpening, it is the body 94 of the drill that is partially ground away. Flutes 92 are grooves that are cut or formed in the body 94 of the drill to allow fluids to reach the point and chips to reach the workpiece surface. Lands 96 are the remaining parts of the outside of the drill body after the flutes 92 are cut. In addition, the drill 99 has an outside diameter d, an axial length h along its axis a.

In use, cutters such as drills perform their function by rotating cutting edges 91 against a material in which a hole is desired. Imparting a torque on the shank 93 causes the rotation of the cutting edges 91. Often either because the length h of the drill may be inadequate to extend the cutting edges 91 to the desired depth of the hole, or because the shank 93 is broken or too short, it is desirable to braze onto the shank an extension.

Advantageously, shanks 93 are readily extended by brazing an extending shaft to the shank 93. In some instances, however, brazing a joint between the extending shaft (not shown) and the drill shank 93 may not produce a joint adequate to withstand the torque necessary to rotate the cutting edges 91 against the material. Failure of such a brazed joint is undesirable for a number of reasons. Therefore, methods and apparatus for torque-testing of brazed drill bits to test the brazed joint to determine its adequacy for suitable operation of the extended drill would have utility.

SUMMARY

The present invention is directed to methods and apparatus for torque-testing of brazed joints for use with drill bits and the like. Embodiments of the invention advantageously permit a torque to be imparted on a substantially cylindrical tool, such as a drill, cutter, or other type of tool, and may be used to test a brazed joint to ensure the suitability of the tool for manufacturing operations.

In one embodiment an apparatus for applying a torque to a tool having a shank includes a base, first and second clamping collars coupled to the base, and a torque-transmitting device. The first clamping collar has a first fixed member coupled to the base and a first floating member operatively coupled to the first fixed member, the first fixed member and the first floating member being engageable to securely clamp a first portion of the tool therebetween. Similarly, the second clamping collar has a second fixed member coupled to the base at a location spaced apart from the first fixed member, and a second floating member operatively coupled to the second fixed member, the second fixed member and the second floating member being engageable to securely clamp a second portion of the tool therebetween. The torque-transmitting device includes a chuck coupleable to the shank of the tool, and an engagement member coupled to the chuck and adapted to be coupled to a torque-providing member.

In another embodiment, a testing torque may be imparted to a cylindrical tool while the tool is clamped in a clamping appliance. The tool has a driven end including a shank and a working end in opposed relation along the axis. The clamping appliance is configured to clamp the tool to prevent rotation of the tool. A shank of the tool is clamped in a chuck. The chuck has a adapter defining a void configured to engagingly receive a socket drive shaft. A torque wrench having a lever arm and a socket driver shaft is engaged by insertion of the socket drive shaft into the void. A torque is imparted to the cylindrical tool about its axis by suitably imparting a force on the lever arm. The quantum of torque imparted is measured based upon operation of the torque wrench.

BRIEF DESCRIPTION OF THE DRAWINGS

Embodiments of the present invention are described in detail below with reference to the following drawings.

DETAILED DESCRIPTION

The present invention relates to methods and apparatus for torque-testing of brazed joints for use with drill bits and the like. Many specific details of certain embodiments of the invention are set forth in the following description and in FIGS. 2 through 4 to provide a thorough understanding of such embodiments. One skilled in the art, however, will understand that the present invention may have additional embodiments, or that the present invention may be practiced without one or more of the details described in the following description.

Figure 2:
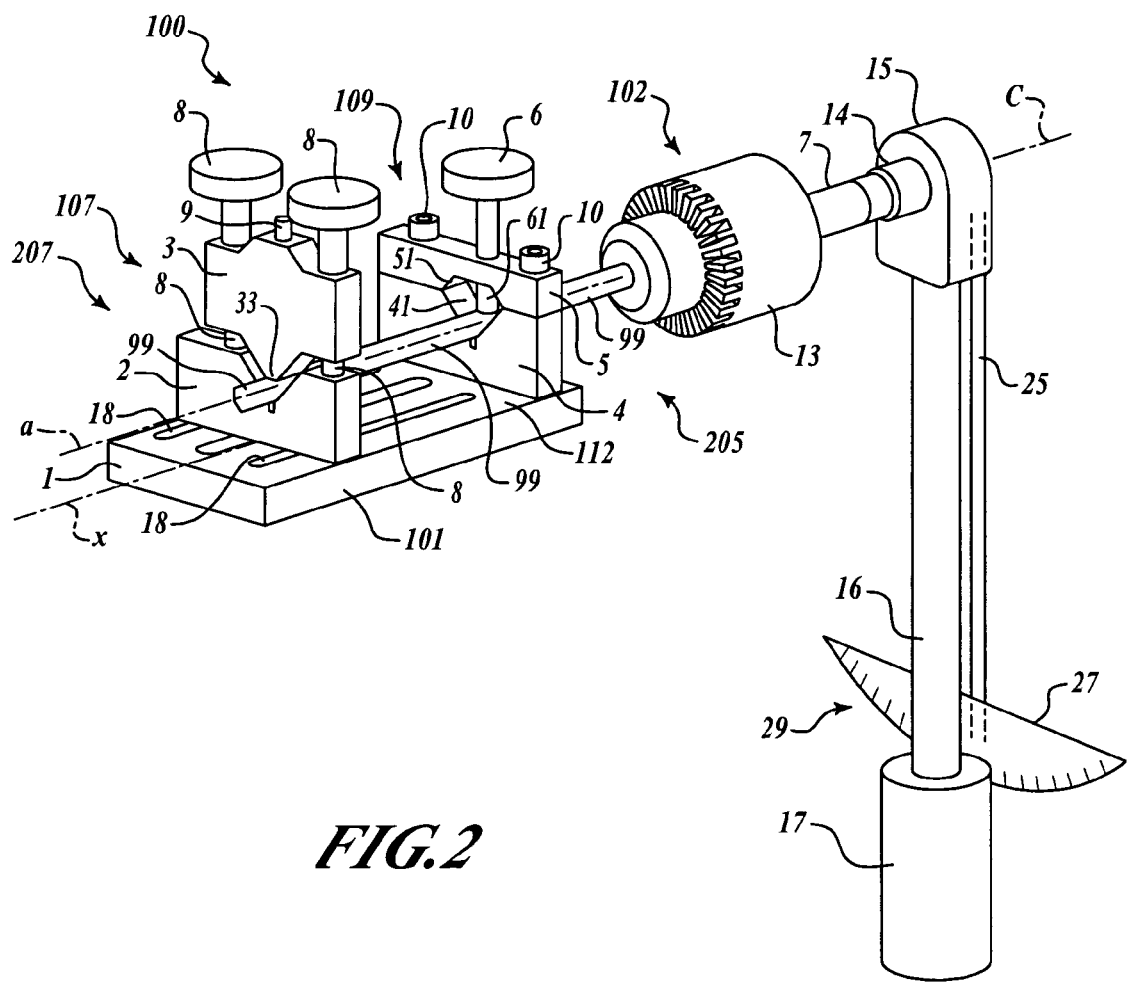
FIG. 2 is an upper isometric view of an apparatus for torque testing a rotating tool in accordance with an embodiment of the invention.
Figure 3:
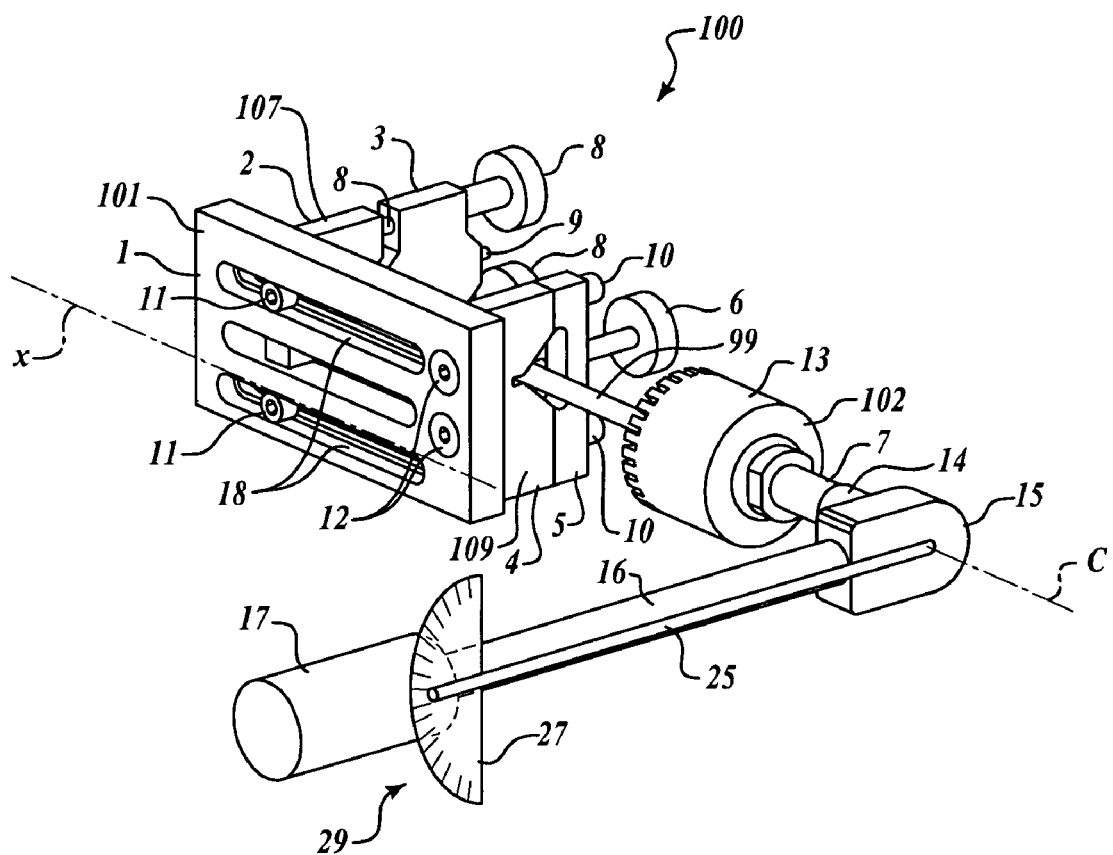
FIG. 3 is a lower isometric view of the apparatus for torque testing a rotating tool of FIG. 2.

Referring the FIGS. 2 and 3, a torque-testing apparatus 100 includes a vise assembly 101 and a chuck assembly 102. The vise assembly 101 includes a first clamping collar 109 and the second clamping collar 107. The chuck assembly 102 includes a chuck 13. The chuck 13 is configured to clamp the drill (or other tool) 99 such that the axis a is substantially collinear with a chuck axis c. The chuck assembly 102 has a adapter 7. The adapter 7 defines a void configured to engagingly receive a drive shaft 14. The drive shaft 14 may be of the type generally found on socket wrenches, including as on a torque wrench 15.

The torque wrench 15 is a device that may be used to precisely set the torque of a fastener, such as a nut or bolt. The torque wrench 15 may be configured with a ratcheting head (e.g. similar to that of a socket wrench) with associated internal mechanisms. Alternately, the torque wrench may be a standard, non-ratcheting type, a production type configured to apply a single, known amount of torque, an adjustable torque wrench that may be adjusted to apply a variable amount of torque, or any other suitable type of torque wrench. Suitable torque wrenches that may be used with the apparatus 100 include those torque wrenches commercially available from Torque Master Tools Pvt. Ltd. of Panchkula, India, or from Torquetech Industrial Equipment & Systems of Mumbai, India, or from BMF Torque Wrench Co. of Huntington Beach, Calif.

In the embodiment shown in FIG. 2, the torque wrench 15 includes a long lever arm 16 between a handle 17 and the drive shaft 14, and made of a material which will bend elastically under an applied torque. A second bar 25 extends approximately parallel with the lever arm 16 to an indicator 27 that is coupled to the lever arm 16 (or handle 17). A calibrated scale 29 is provided on the indicator 27, so that as torque is applied using the lever arm 16, the second bar 25 moves along the calibrated scale 29 to indicate the amount of torque being applied by the drive shaft 14. Of course, a variety of alternate embodiments of torque wrenches may be used.

In one particular embodiment, the torque wrench 15 includes a calibrated clutch mechanism. At the point where the desired torque is reached, the clutch slips, preventing overtightening. The most common form uses a ball detent and spring, with the spring preloaded by an adjustable screw thread, calibrated in torque units. The ball detent transmits force until the preset torque is reached, at which point the force exerted by the spring is overcome and the ball "clicks" out of its socket. An advantage of this design is greater precision and a positive action at the set point. A number of variations of this design exist for different applications and different torque ranges, and are commercially available from one or more of the above-referenced suppliers.

Referring to FIG. 2, the first clamping collar 109 is configured to clamp the body 94 (see FIG. 1) of the drill 99. To suitably clamp the body 94 of the drill 99, by means of non-limiting example, the first clamping collar 109 includes a first fixed jaw 4 and a first floating jaw 5. The first fixed jaw 4 is configured such that the drill 99 rests upon the first fixed jaw 4 on a first engaging surface 41. The floating jaw 5 is moved translationally into engagement with the fixed jaw 4 in order to clampingly hold the drill 99 in a fixed alignment within the first clamping collar 109 between the first fixed jaw 4 and the first floating jaw 5.

To move the first floating jaw 5 into engagement with the fixed jaw 4, a pair of tightening screws 10 are configured to motivate the floating jaw 5 upon rotation of the tightening screws 10. Additionally, an optional first thumbscrew (or registration member) 6 is threaded through the first floating jaw 5 such that rotation of the first thumbscrew 6 extends an end 61 of the first thumbscrew 6 from the first floating jaw 5 until it bears at a bearing surface 61 against the drill 99 to suitably clamp the drill 99 such that the axis a is parallel (or collinear) with the chuck axis c.

To further facilitate the insertion of the drill 99 into the first clamping collar 109, a keyway 51 is cut into the first floating jaw 5. The keyway 51 is configured, in one embodiment, as a "V"-shaped engaging surface to cradle the drill 99 in clamped engagement.

Like the first clamping collar 109, the second clamping collar 107 includes floating and fixed jaws. More specifically, a second floating jaw 3, moves translationally into and out of engagement with a second fixed jaw 2. Similarly, the jaws 2, 3 are configured to hold the body 94 of the drill 99 such that the axis a is parallel (or collinear) with the chuck axis c. The first and second fixed jaws 4, 2 are coupled to a base 1 having a plurality of elongated slots 18 formed therein. The second fixed jaw 2 of the second clamping collar 107 may be configured to selectably move along the elongated slots (or races) 18 to allow the distance between the first and second fixed jaws 4, 2 to be adjusted along an axis x of the base 1 to suitably accommodate drills 99 (or other tools) of differing lengths h (FIG. 1).

To urge the second floating jaw 3 into engagement with the second fixed jaw 2, two second thumbscrews 8 having shoulders to bear against the second floating jaw 3 are threaded and configured such that the rotation of the second thumbscrews 8 draws the second floating jaw 3 into engagement with the second fixed jaw 2. Optionally, a first setscrew (or registration member) 9 may be included to extend upon rotation into locking engagement with the body 94 (FIG. 1) thereby preventing rotation about the axis a when a torque is applied to the drill 99.

As shown in FIG. 3, the first fixed jaw 4 of the first clamping collar 109 is coupled to the base 1 by a pair of fasteners 12. In this embodiment, the first clamping collar 109 is positioned proximate the first end of the base 1. A pair of second setscrews 11 project through the elongated slots 18 to engage with the second fixed jaw 2. When loosened, the setscrews 11 permit the second fixed jaw 2 (and thus the second clamping collar 107) to translate along the slots 18. Alternately, when tightened, the second fixed jaw 2 is held in stationary position on the base 1. The second setscrews 11 are threadedly engaged with the second fixed jaw 2 thereby allowing the second clamping collar 107 to slide appropriately to accommodate tools 99 of differing lengths. When suitably adjusted, the second setscrews 11 are suitably tightened to lock the second clamping collar 107 in fixed relation to the first clamping collar 109 thereby to suitably fix the drill 99 against the imparted torque of the torque wrench 15. In alternate embodiments, both the first and second fixed jaws 4, 2 may be moveably coupled to the slots 18, or the first fixed jaw 2 may be moveably coupled to the base 1 and the second fixed jaw 4 may be fixedly coupled to the base 1.

Figure 1:
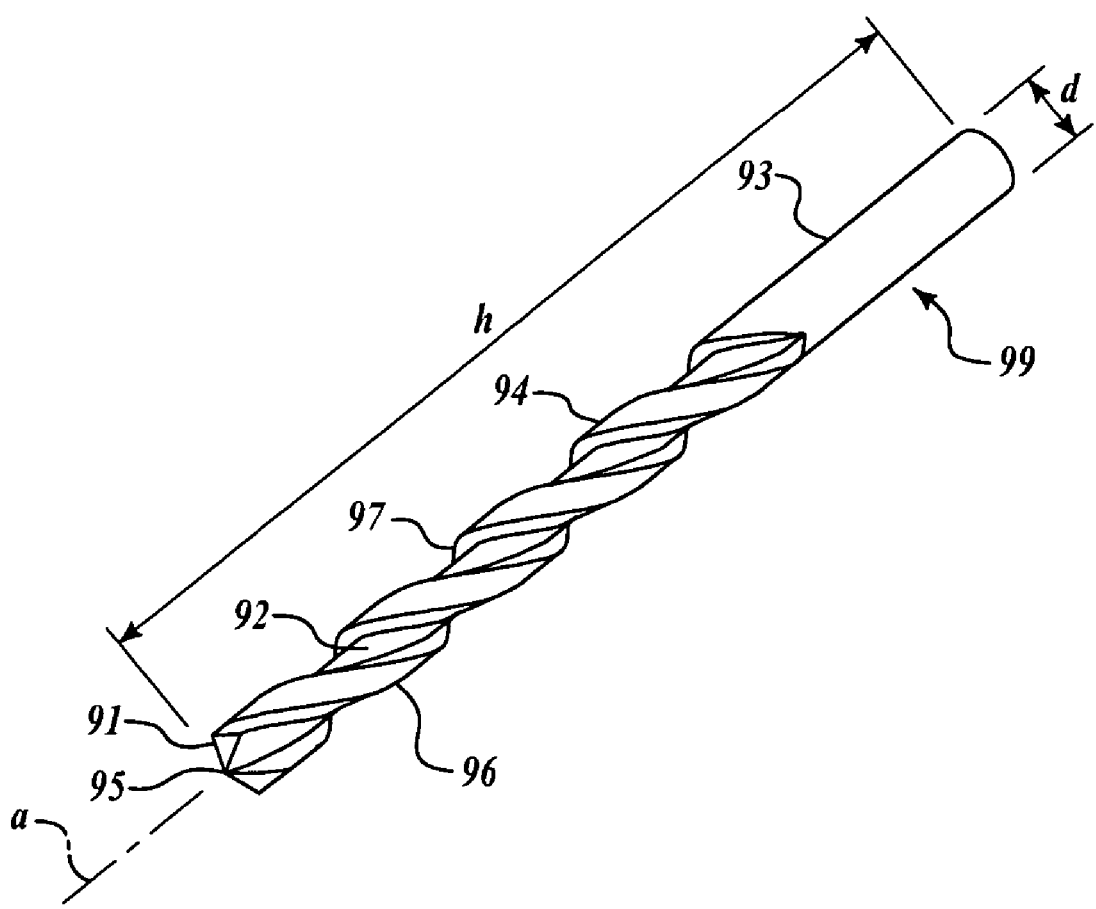
FIG. 1 is a plan view of a prior art cutting tool.

In operation, once the body 94 of the drill 99 is suitably clamped in the vise assembly 101, the shank 93 of the drill 99 is inserted into the chuck 13, which is tightened to clamp to the shank 93 (FIG. 1). The chuck 13 is coupled to the adapter 7. The torque wrench 15 imparts a torque upon the drill 99, the applied torque being measurable by the torque wrench 15. In a proof mode of operation, a measured torque is imparted by the torque wrench 15 in order to test if the drill 99 will remain intact in the presence of such an imparted torque. Alternately, in a test mode of operation, the imparted torque is applied in gradually increasing application. The torque necessary to induce the failure of the drill 99 is recorded and thereby the failure of the tool is studied.

Figure 4:
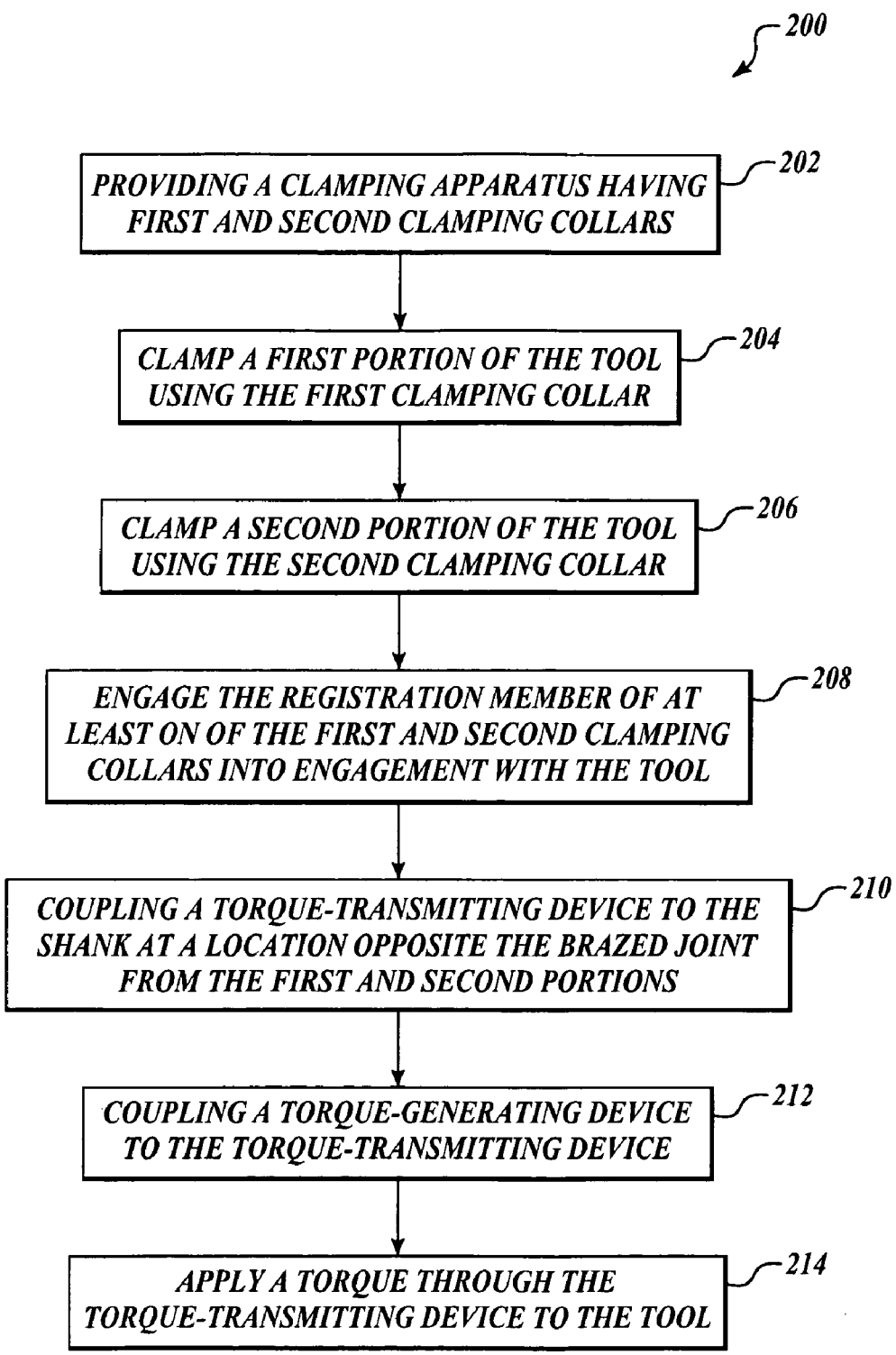
FIG. 4 is a flowchart showing a method of torque-testing a tool having a shank that includes a brazed joint in accordance with another embodiment of the invention.

FIG. 4 is a flowchart showing a method 200 of torque-testing a tool having a shank that includes a brazed joint in accordance with another embodiment of the invention. In this embodiment, at a block 202, the method 200 includes providing a clamping apparatus having a first clamping collar adapted to securely clamp a first portion of the tool, and a second clamping collar adapted to securely clamp a second portion of the tool. The first and second portions of the tool are spaced apart and on a first side of the brazed joint, and the first and second clamping collars are adapted to prevent rotation of the tool. At a block 204, the first portion of the tool is clamped using the first clamping collar, and the second portion of the tool is clamped using the second clamping collar at a block 206.

In one particular embodiment, the first clamping collar is arranged to intersect a first orientation plane 205 (FIG. 2) and is configured to clamp a substantially cylindrical tool in a clamping position such that an axis a (FIG. 2) of the tool is held substantially perpendicular to the first orientation plane. Similarly, in a particular embodiment, the second clamping collar is spaced apart from the first clamping collar and is arranged to intersect a second orientation plane 207 approximately parallel to the first orientation plane 205 (FIG. 2) and is configured to clamp the substantially cylindrical tool in the clamping position such that the axis a is held substantially perpendicular to the second orientation plane.

As further shown in FIG. 4, at a block 208, a registration member (or screw) of at least one of the first and second clamping collars is rotated to frictionally engage the registration member against the tool. As best shown in FIG. 2, the registration member may be located on the first clamping collar (e.g. thumbscrew 6), or the second clamping collar (e.g. set screw 9), or both. Although specific examples of suitable registration members are described above and shown in FIGS. 2 and 3, it may be appreciated that any other suitable type of registration member may be used.

The method 200 further includes coupling a torque-transmitting device to the shank at a location opposite the brazed joint from the first and second portions at a block 210. In one particular embodiment, the coupling of the torque-transmitting device to the shank includes coupling a chuck to the shank such that an axis of the tool is substantially collinear with an axis of the chuck. The torque-transmitting device may include a adapter defining a void configured to engagingly receive a socket drive shaft. At a block 212, a torque-generating device may be coupled to the torque-transmitting device. For example, in a particular embodiment, a socket drive shaft of a torque wrench is engaged into the void in the adapter.

At a block 214, a torque is applied through the torque-transmitting device to the tool. In one embodiment, the torque is applied through the torque-transmitting device using a torque wrench. In one particular embodiment, the torque applied through the torque-transmitting device is a maximum torque specified for operation of the tool. Thus, the strength of the brazed joint of the tool may be tested and properly verified prior to use.

Embodiments of methods and apparatus for torque-testing of brazed joints in accordance with the present invention may provide significant advantages over the prior art. For example, embodiments of the invention advantageously permit a torque to be inparted on a substantially cylindrical tool, such as a drill, cutter, or other type of tool, allowing a brazed joint to be properly tested prior to use to ensure the suitability of the tool for manufacturing operations. Embodiments of the invention are relatively economical to construct and operate, and relatively simple to use, and may thereby reduce costs and increase productivity.

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. An apparatus for applying a torque to a tool having a shank, comprising:
   a base;
   a first clamping collar having a first fixed member coupled to the base and a first floating member operatively coupled to the first fixed member, the first fixed member and the first floating member being engageable to securely clamp a first portion of the tool therebetween;
   a second clamping collar having a second fixed member coupled to the base at a location spaced apart from the first fixed member, and a second floating member operatively coupled to the second fixed member, the second fixed member and the second floating member being engageable to securely clamp a second portion of the tool therebetween; and
   a torque-transmitting device including a chuck coupleable to the shank of the tool, and an engagement member coupled to the chuck and adapted to be coupled to a torque-providing member.

2. The apparatus of claim 1, wherein the base has a plurality of elongated slots disposed therein, and wherein at least one of the first and second fixed members is moveably coupled to the base by fasteners passing through the slots.

3. The apparatus of claim 1, wherein the engagement member comprises a void adapted to receive a projecting portion of the torque-providing member.

4. The apparatus of claim 1, wherein the first fixed member and the first floating member each has a first notch formed therein, the first notches being opposingly alignable such that the first portion of the tool is securely clamped between the first notches, and wherein the second fixed member and the second floating member each has a second notch formed therein, the second notches being opposingly alignable such that the second portion of the tool is securely clamped between the second notches.

5. The apparatus of claim 4, further comprising:
   a first setscrew threadedly engaged through the first floating member and adapted to project through the first notch thereof and to bear against the first portion of the tool; and
   a second setscrew threadedly engaged through the second floating member and adapted to project through the second notch thereof and to bear against the second portion of the tool.

6. An appliance for applying a torque to a tool having a shank, comprising:
   an elongated base having a first end and a second end and an axis extending between the first and second ends;
   a first fixed jaw coupled to the base proximate the first end, the first fixed jaw defining at least one first bore internally threaded to engagedly receive a first threaded screw, the first fixed jaw having a first clamping surface;
   a second fixed jaw coupled to the base and spaced apart from the first fixed jaw, the second fixed jaw defining at least one second bore internally threaded to engagedly receive a second threaded screw, the second fixed jaw having a second clamping surface;

a first floating jaw operatively coupled to the first fixed jaw and defining at least one third bore configured to slidingly receive the first threaded screw, the first floating jaw having a third clamping surface configured to engage the first clamping surface;

a second floating jaw operatively coupled to the second fixed jaw and defining at least one fourth bore configured to slidingly receive the second threaded screw, the second floating jaw having a fourth clamping surface configured to engage the second clamping surface;

at least one first tightening screw configured to slidingly pass through the third bore and to threadedly engage the first threaded bore such that rotation of the first tightening screw urges the third clamping surface toward the first clamping surface to clamp a first portion of the tool;

at least one second tightening screw configured to slidingly pass through the fourth bore and to threadedly engage the second threaded bore such that rotation of the second tightening screw urges the fourth clamping surface toward the second clamping surface to clamp a second portion of the tool; and a torque-transmitting device including a chuck adapted to be coupled to the shank of the tool, and an engagement member coupled to the chuck and adapted to be coupled to a torque-providing member.

7. The appliance of claim 6, wherein:
the base further defines at least one slot elongated parallel to the axis; and
the second fixed jaw is further configured to engage the slot such that the second fixed jaw is moveably coupled to the base and is configured to move translationally along the slot.

8. The appliance of claim 6, wherein:
the first clamping surface defines a V-shaped profile and the third clamping surface defines a truncated V-shaped profile configured to substantially engage the first clamping surface; and
the second clamping surface defines a V-shaped profile and the fourth clamping surface defines a truncated V-shaped profile configured to substantially engage the second clamping surface.

9. The appliance of claim 6, wherein the tool has a tool axis, and wherein
the first fixed jaw and the first floating jaw comprise a first clamping collar arranged to intersect a first orientation plane and configured to clamp the tool such that the tool axis is held substantially perpendicular to the first orientation plane; and
the second fixed jaw and the second floating jaw comprise a second clamping collar arranged to intersect a second orientation plane parallel to the first orientation plane and configured to clamp the tool such that the tool axis is held substantially perpendicular to the second orientation plane.

10. The appliance of claim 9, wherein:
the first floating jaw is configured to move translationally within the first orientation plane with respect to the first fixed jaw; and
the second floating jaw is configured to move translationally within the second orientation plane with respect to the second fixed jaw.

11. The appliance of claim 6, further comprising:
at least one registration member threadedly disposed through at least one of the first and second floating jaws and configured to engage the tool to prevent rotation of the tool.

12. The appliance of claim 6, wherein the tool has a tool axis and the chuck has a chuck axis substantially collinear with the tool axis.

13. The appliance of claim 6, wherein the engagement member includes a adapter defining a void configured to engagingly receive a socket drive shaft.

14. A method for testing a tool having a shank including a brazed joint, comprising:
providing a clamping apparatus having a first clamping collar adapted to securely clamp a first portion of the tool and a second clamping collar adapted to securely clamp a second portion of the tool, the first and second portions of the tool being spaced apart and on a first side of the brazed joint, the first and second clamping collars being adapted to prevent movement of the tool;
clamping the first portion of the tool using the first clamping collar;
clamping the second portion of the tool using the second clamping collar;
coupling a torque-transmitting device to the shank opposite the brazed joint from the first and second portions; and
applying a torque through the torque-transmitting device to the tool.

15. The method of claim 14, wherein coupling the torque-transmitting device to the shank includes coupling a chuck to the shank such that an axis of the tool is substantially collinear with an axis of the chuck and having a adapter defining a void configured to engagingly receive a socket drive shaft.

16. The method of claim 14, wherein coupling the torque-transmitting device to the shank includes coupling a chuck to the shank, the chuck having a adapter defining a void configured to engagingly receive a socket drive shaft.

17. The method of claim 16, further comprising engaging a socket drive shaft of a torque wrench into the void in the adapter, and wherein applying a torque through the torque-transmitting device includes applying a torque through the torque-transmitting device using the torque wrench.

18. The method of claim 16, wherein at least one of the first and second clamping collars includes a set screw configured to bear against the tool, the method further comprising rotating the set screw to frictionally engage the tool.

19. The method of claim 16, wherein providing a clamping apparatus includes providing a clamping apparatus having:
a first clamping collar arranged to intersect a first orientation plane and configured to clamp a substantially cylindrical tool, the tool having an axis, in a clamping position such that the axis is held substantially perpendicular to the first orientation plane; and
a second clamping collar spaced apart from the first clamping collar arranged to intersect a second orientation plane parallel to the first orientation plane and configured to clamp the substantially cylindrical tool in the clamping position such that the axis is held substantially perpendicular to the second orientation plane.

20. The method of claim 16, wherein applying a torque through the torque-transmitting device includes applying a maximum torque specified for operation of the tool.

* * * * *